(12) United States Patent
Ananthan

(10) Patent No.: US 7,105,675 B2
(45) Date of Patent: Sep. 12, 2006

(54) PYRIDOMORPHINANS, THIENOMORPHINANS AND USE THEREOF

(75) Inventor: Subramaniam Ananthan, Birmingham, AL (US)

(73) Assignee: Southern Research Institute, Birmingham, AL (US)

(*) Notice: Subject to any disclaimer, the term of this patent is extended or adjusted under 35 U.S.C. 154(b) by 0 days.

(21) Appl. No.: 11/259,073

(22) Filed: Oct. 27, 2005

(65) Prior Publication Data

US 2006/0047119 A1    Mar. 2, 2006

Related U.S. Application Data

(62) Division of application No. 10/049,504, filed as application No. PCT/US00/22094 on Aug. 14, 2000, now Pat. No. 7,015,326.

(60) Provisional application No. 60/148,581, filed on Aug. 13, 1999.

(51) Int. Cl.
    *C07D 498/20* (2006.01)
(52) U.S. Cl. .................................... 546/40
(58) Field of Classification Search ............ 546/40
    See application file for complete search history.

(56) References Cited

U.S. PATENT DOCUMENTS

| 4,816,586 A | 3/1989 | Portoghese |
| 5,223,507 A | 6/1993 | Dappen et al. |

FOREIGN PATENT DOCUMENTS

WO    WO-96/02545    2/1996

*Primary Examiner*—Patricia L. Morris
(74) *Attorney, Agent, or Firm*—Connolly, Bove, Lodge & Hutz, LLP

(57) ABSTRACT

Compounds represented by the formulae:

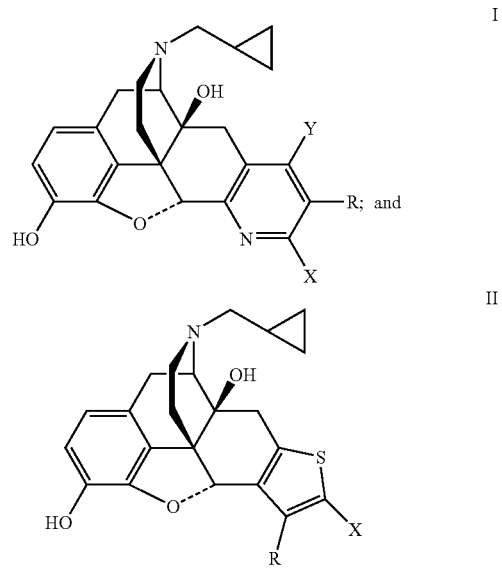

wherein each of Y, X and R individually is selected from the group consisting of hydrogen, hydroxy, halo, $CF_3$, $NO_2$, CN, $NH_2$, $COR^1$ and $CO_2R^2$ wherein $R^1$ is selected from the group consisting of alkyl, aryl, alkaryl, and $NH_2$, and $R^2$ is selected from the group consisting of alkyl, aryl and aralkyl, and provided that at least one of Y, X and R is other than H; and pharmaceutically acceptable salts thereof are provided. Compounds of the above formula are useful as analgesics for treating pain, as immunomodulators and for treating drug abuse.

6 Claims, No Drawings

PYRIDOMORPHINANS, THIENOMORPHINANS AND USE THEREOF

This application is a Divisional of U.S. application Ser. No. 10/049,504, filed Jun. 18, 2002 now U.S. Pat. No. 7,015,326 which is a National Stage of PCT/US00/22094 filed Aug. 14, 2000 which in turn claims priority from U.S. Provisional Application 60/148,581, filed Aug. 13, 1999.

FEDERALLY SPONSORED RESEARCH OR DEVELOPMENT

This invention was made under Grant DA 08883 from the National Institute on Drug Abuse.

TECHNICAL FIELD

The present invention relates to certain pyridomorphinan and thienomorphinan compounds and more particularly to naltrexone-derived pyridomorphinan and thienomorphinan compounds. Compounds of the present invention exhibit high antagonist activity at the δ receptor. Moreover, various compounds of the present invention possess μ agonist characteristics. Compounds of the present invention are especially useful as analgesics for treating patients suffering from pain, useful as drugs to modulate the development of tolerance and dependence to μ agonists, modulate the behavioral effects of drugs of abuse, and to elicit immunomodulatory effects.

BACKGROUND OF INVENTION

Opioid receptors belong to the superfamily of G-protein coupled receptors that mediate the analgesic and other pharmacological actions of morphine and related opioid drugs. In the past, it was believed that only a single opioid binding site existed. The existence of at least three distinct subtypes of opioid receptors, designated μ, δ and κ receptors, in the central nervous system and periphery is now well established. Human μ, δ and κ receptors have been cloned and have been shown to belong to the G protein-coupled receptor (GPCR) superfamily.

The existence of three distinct opioid receptor types, μ, δ and κ, is confirmed by the recent cloning of these three opioid receptors from mouse, rat and human cDNAs. All three of the opioid receptor types are located in human brain or spinal cord tissues and each has a role in the mediation of pain. Opiates are used extensively for the treatment of pain and are the most effective analgesic agents available. Morphine and its analogues currently prescribed as potent analgesics are μ selective ligands. The general administration of these medications is limited by side-effects such as respiratory depression, depression of gastrointestinal motility and development of tolerance and physical dependence.

The development of potent and selective antagonist and agonist ligands for each of these opioid receptor subtypes has been the goal of medicinal chemists for many years because of their potential usefulness as pharmacological tools and as therapeutic agents. Among the μ, δ and κ receptors, the development of antagonist and agonist ligands acting through the δ receptor has become the focus of research in recent years due to the therapeutic potential of opioid δ ligands. Various studies suggest that δ selective agonists could be potentially useful as analgesics devoid of side effects such as respiratory depression and physical dependence side effects. Selective antagonists of δ receptors have been shown to display immunomodulatory effects as well as modulatory effects on the actions of drugs of abuse such as cocaine and methamphetamines. Moreover, recent studies using rodents have demonstrated that δ opioid antagonists are capable of preventing the development of tolerance and dependence to μ agonist such as morphine without interfering with the μ opioid antinociception.

It has been found that a number of ligands synthetically derived from naltrexone display significant selectivity toward the δ receptors. Among these, the indolomorphinan naltrindole is presently widely used as δ selective antagonist ligand, and other ligands such as its 5'-isothiocyanate derivative, benzofuran analog, and (E)-7-benzylidenenaltrexone have been useful in the pharmacological characterization of δ opioid receptor subtypes.

Continuing efforts exist for developing subtype selective nonpeptide opioid ligands.

SUMMARY OF INVENTION

The present invention relates to compounds represented by the following formulae:

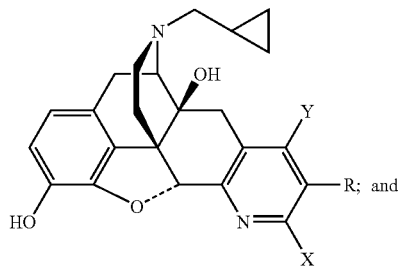

wherein each of Y, X and R is individually selected from the group consisting of hydrogen, hydroxy, alkyl, alkoxy, aryl, halo, $CF_3$, $NO_2$, CN, $NH_2$, $COR^1$ and $CO_2R^2$, wherein $R^1$ is selected from the group consisting of alkyl, aryl, aralkyl and $NH_2$; and $R^2$ is selected from the group consisting of alkyl, aryl and aralkyl; and provided that at least one of Y, X and R in formula I is other than hydrogen; and pharmaceutically acceptable salts thereof.

The present invention also relates to treating a patient suffering from pain which comprises administering to the patient a pain treating effective amount of at least one of the above compounds.

A further aspect of the present invention relates to treating a patient in need of an immunomodulatory agent which comprises administering to the patient an immunomodulatory effective amount of at least one of the above compounds.

A still further aspect of the present invention relates to treating a patient suffering from drug abuse which comprises administering an effective amount for treating drug abuse of at least one of the above compounds.

Another aspect of the present invention is concerned with treating a patient suffering from dependence on or tolerance to a μ agonist which comprises administering to the patient at least one of the above compounds in an amount effective to modulate the tolerance to or dependence on μ agonists, such as morphine.

Still other objects and advantages of the present invention will become readily apparent to those skilled in the art from the following detailed description, wherein it is shown and described preferred embodiments of the invention, simply by way of illustration of the best mode contemplated of carrying out the invention. As will be realized the invention is capable of other and different embodiments, and its several details are capable of modifications in various obvious respects, without departing from the invention. Accordingly, the description is to be regarded as illustrative in nature and not as restrictive.

BEST AND VARIOUS MODES FOR CARRYING OUT INVENTION

The compounds according to the present invention are represented by the following formulae:

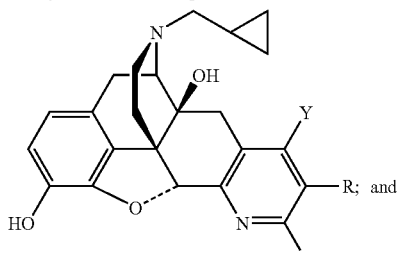

I

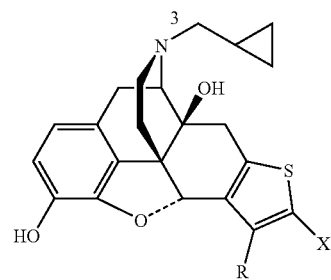

II wherein each of Y, X and R is individually selected from the group consisting of hydrogen, hydroxy, halo, $CF_3$, $NO_2$, CN, $NH_2$, $COR^1$ and $CO_2R^2$ wherein $R^1$ is selected from the group consisting of alkyl, aryl, aralkyl and $NH_2$; and $R^2$ is selected from the group consisting of alkyl, aryl and aralkyl; and provided that at least one of Y, X and R in formula I is other than hydrogen; and pharmaceutically acceptable salts thereof.

The alkyl groups typically contain 1 to about 6 carbon atoms, and more typically 1 to about 3 carbon atoms, and can be straight, branched-chain or cyclic saturated aliphatic hydrocarbon groups.

Examples of suitable alkyl groups include methyl, ethyl and propyl. Examples of branched alkyl groups include isopropyl and t-butyl. Examples of suitable cyclic aliphatic groups typically contain 3–6 carbon atoms and include cyclopentyl and cyclohexyl. Examples of aryl groups are phenyl and naphthyl. Examples of aralkyl groups include phenyl $C_{1-3}$ alkyl such as benzyl.

Pharmaceutically acceptable salts of the compounds of the present invention include those derived from pharmaceutically acceptable, inorganic and organic acids and bases. Examples of suitable acids include hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, formic, benzoic, malonic, naphthalene-2-sulfonic, trifluoroacetic and benzene-sulfonic acids. Salts derived from appropriate bases include alkali such as sodium and ammonium.

The preferred compounds of the present invention represented by formula I contain a R constituent other than hydrogen the preferred compounds of the present invention represented by formula II contain $NH_2$ as the X substituent.

Some specific compounds according to the present invention are the following:

5'-Bromo-17-(cyclopropylmethyl)-6,7-didehydro-3,14-dihydroxy-4,5α-epoxypyrido[2',3':6,7]morphinan (referred to herein also as 7b).

5'-Cyano-17-(cyclopropylmethyl)-6,7-didehydro-3,14-dihydroxy-4,5α-epoxypyrido[2',3':6,7]morphinan (referred to herein also as 7c).

5'-Carbethoxy-17-(cyclopropylmethyl)-6,7-didehydro-3,14-dihydroxy-4,5α-epoxypyrido[2',3':6,7]morphinan (referred to herein also as 7d).

17-(Cyclopropylmethyl)-6,7-didehydro-3,14-dihydroxy-4,5α-epoxy-5'-nitropyrido[2',3':6,7]morphinan (referred to herein also as 7e).

5'-Amino-17-(cyclopropylmethyl)-6,7-didehydro-3,14-dihydroxy-4,5α-epoxypyrido[2',3':6,7]morphinan (referred to herein also as 7f).

5'-Amino-4'-cyano-17-(cyclopropylmethyl)-6,7-didehydro-3,14-dihydroxy-4,5α-epoxythieno [2',3':7,6]morphinan (referred to herein also as 8a).

5'-Amino-4'-carbomethoxy-17-(cyclopropylmethyl)-6,7-didehydro-3,14-dihydroxy-4,5α-epoxythieno[2',3':7,6]morphinan (referred to herein also as 8b).

5'-Amino-4'-carbethoxy-17-(cyclopropylmethyl)-6,7-didehydro-3,14-dihydroxy-4,5α-epoxythieno[2',3':7,6]morphinan (referred to herein also as 8c).

5'-Amino-4'-benzyloxycarbonyl-17-(cyclopropylmethyl)-6,7-didehydro-3,14-dihydroxy-4,5α-epoxythieno[2',3':7,6]morphinan (referred to herein also as 8d).

5'-Amino-4'-aminocarbonyl-17-(cyclopropylmethyl)-6,7-didehydro-3,14-dihydroxy-4,5α-epoxythieno[2',3':7,6]morphinan (referred to herein also as 8e).

5'-Amino-4'-benzoyl-17-(cyclopropylmethyl)-6,7-didehydro-3,14-dihydroxy-4,5α-epoxythieno[2',3':7,6]morphinan (referred to herein also as 8f).

Compounds of the present invention represented by formula I can be synthesized from naltrexone by condensation with, for instance, a substituted acrolein as illustrated in Scheme 1 below.

By way of example, 5'-bromo-, 5'-cyano-, and 5'-carbethoxypyridomorphinans (referred to herein below as 7b–d) were synthesized by using the corresponding 2-bromo-, 2-cyano-, or 2-carbethoxy-3-(dimethylamino)acroleins in the condensation reaction with naltrexone (Scheme 1).

Methods for producing the acrolein intermediates used for synthesis of pyridomorphinans of the present invention are known. For example, Gais et al, Acetylenes with Electron-Donor and Electron-Acceptor Groups, Helv. Chim. Acta. 1969, 52, 2641–2657, describes a procedure for making 2-bromo-3-(dimethylamino)acrolein. Reichardt et al, Vilsmeier-Formylation of Acetonitrile 1970, 538 discloses a procedure for making 2-cyano-3-(dimethylamino)acrolein. Kim et al, A New Synthesis of 5,7-Dicarboxy-2,1-benzisoxazolin-3-one, J. Heterocyclic Chem. 1985, 22, 127–128 describes methodology for making 2-carbethoxy-3(dimethylamino)acrolein.

In addition, compounds referred to hereinbelow as 7e and 7f were synthesized by modifying the method described by Tohda et al, Nucleophilic Reaction upon Electron-Deficient Pyridone Derivatives X. One-Pot Synthesis of 3-Nitropyridines by Ring Transformation of 1-Methyl-3,5-dinitro-2-pyridone with Ketones or Aldehydes in the Presence of Ammonia, Bull. Chem. Soc. Jpn. 1990, 63, 2820–2827, for producing nitropyridine by using 3,5 dinitro-1-methyl-2-pyridone which produced the nitro compound 7e which was reduced to the amine 7f.

Scheme 1

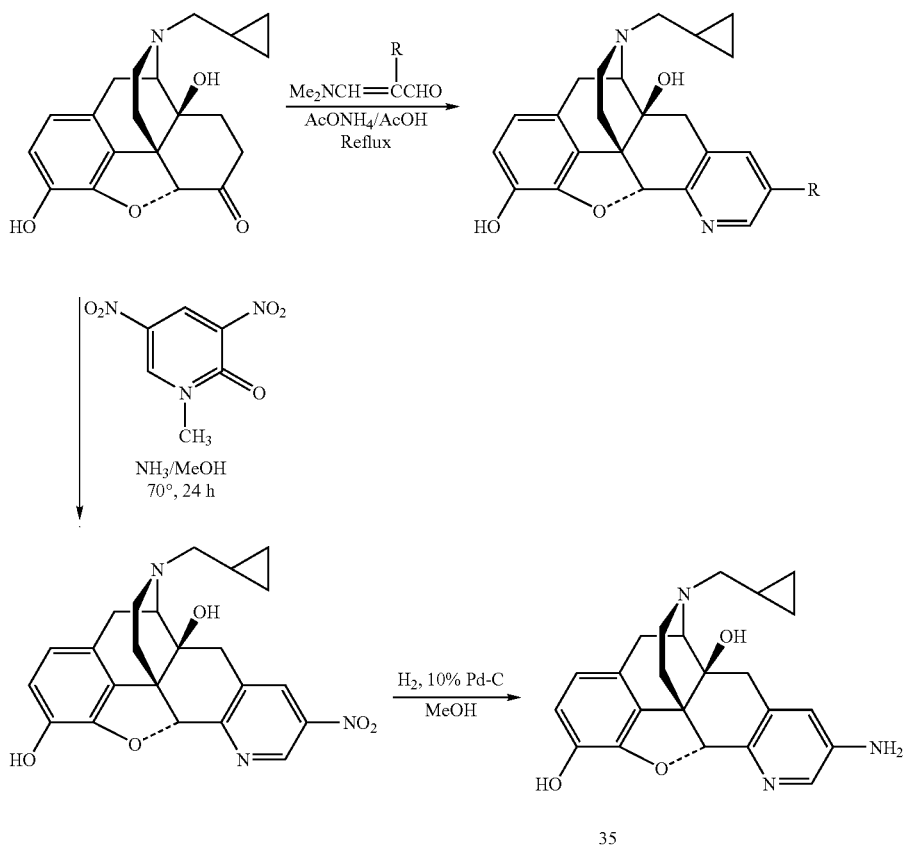

Compounds of the present invention represented by formula II can be synthesized from naltrexone by condensation with active methylene nitriles and elemental sulfur in the presence of a base as illustrated by Scheme 2 below. This is a modification of a reaction scheme for synthesizing thiophenes described by Gewald et al, 2-Aminothiophenes from Active Methylene Nitriles, Carbonyl Compounds and Sulfur, *Chem. Ber.* 1966, 99, 94–100.

Scheme 2

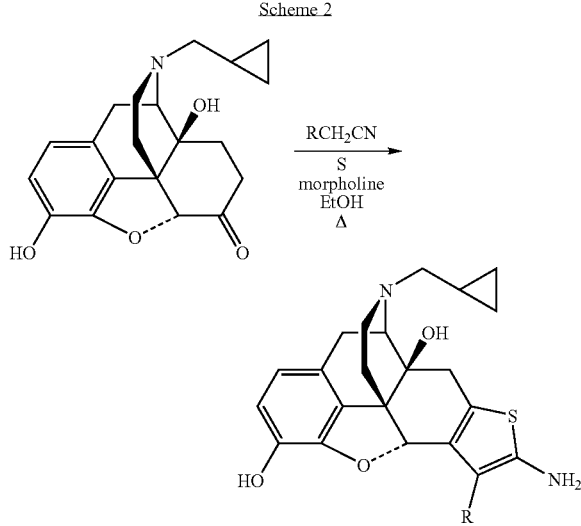

The following non-limiting examples are presented to further illustrate the present invention.

EXAMPLE 1

Preparation of 5'-Bromo-17-(cyclopropylmethyl)-6,7-didehydro-3,14-dihydroxy-4,5α-epoxypyrido[2',3':6,7]morphinan (7b).

A mixture of naltrexone (1.0 g, 2.9 mmol), 2-bromo-3-(dimethylamino)acrolein (1.04 g, 5.9 mmol) and ammonium acetate (0.92 g, 12.0 mmol) in glacial acetic acid (15 mL) was heated under reflux under an atmosphere of argon for 3 days. The acetic acid was removed under reduced pressure and the residue was treated with water and the mixture was made basic with concentrated aqueous $NH_4OH$. The mixture was extracted with $CH_2Cl_2$ (3×80 mL). The combined organic extracts were washed with brine, dried ($Na_2SO_4$) and the solvent was removed under reduced pressure. The residue was purified by flash chromatography over a column of silica using $CHCl_3$-MeOH (99.5:0.5) followed by $CHCl_3$-MeOH—$NH_4OH$ (99:0.5:0.5) as the eluent to obtain 7b (0.212 g): mp 266–268° C. dec; TLC, $R_f$ 0.43 ($CHCl_3$-MeOH—$NH_4OH$, 95:5:0.5).

EXAMPLE 2

Preparation of 5'-Cyano-17-(cyclopropylmethyl)-6,7-didehydro-3,14-dihydroxy-4,5α-epoxypyrido[2',3':6,7]morphinan (7c).

A mixture of naltrexone (1.0 g, 2.9 mmol), 2-cyano-3-(dimethylamino)acrolein (0.73 g, 5.9 mmol) and ammonium acetate (0.92 g, 12.0 mmol) in glacial acetic acid (15 mL) was heated under reflux under an atmosphere of argon for 3 days. The acetic acid was removed under reduced pressure and the residue was treated with water and the pH of the mixture was adjusted to 8 with concentrated aqueous $NH_4OH$. The mixture was extracted with $CH_2Cl_2$ (3×80 mL). The combined organic extracts were washed with brine, dried ($Na_2SO_4$) and the solvent was removed under reduced pressure.

The residue was purified by flash chromatography over a column of silica using $CHCl_3$-MeOH—$NH_4OH$ (98.5:1.0: 0.5) as the eluent to obtain 7c (0.142 g): mp 152–158° C. dec; TLC, $R_f$ 0.21 ($CHCl_3$-MeOH—$NH_4OH$, 95:5:0.5).

EXAMPLE 3

Preparation of 5'-Carbethoxy-17-(cyclopropylmethyl)-6,7-didehydro-3,14-dihydroxy-4,5α-epoxypyrido[2',3':6,7]morphinan (7d).

A mixture of naltrexone (1.0 g, 2.9 mmol), 2-carbethoxy-3-(dimethylamino)acrolein (1.0 g, 5.9 mmol) and ammonium acetate (0.92 g, 12.0 mmol) in glacial acetic acid (15 mL) was heated under reflux under an atmosphere of argon for 30 h. The acetic acid was removed under reduced pressure and the residue was treated with water and the pH of the mixture was adjusted to 8 to 9 with saturated aqueous $NaHCO_3$. The mixture was extracted with $CH_2Cl_2$ (4×150 mL).

The combined organic extracts were washed with brine, dried ($Na_2SO_4$) and the solvent was removed under reduced pressure.

The residue was purified by flash chromatography over a column of silica using $CHCl_3$-EtOH—$NH_4OH$ (98.5:1.0: 0.5) as the eluent to obtain 7d (0.503 g): mp 138–145° C. dec; TLC, $R_f$ 0.29 ($CHCl_3$-MeOH—$NH_4OH$, 95:5:0.5).

EXAMPLE 4

Preparation of 17-(cyclopropylmethyl)-6,7-didehydro-3,14-dihydroxy-4,5α-epoxy-5'-nitropyrido[2',3':6,7]morphinan (7e).

A stirred solution of naltrexone (4.26 g, 12.4 mmol), 1-methyl-3,5-dinitropyridin-2-one (2.99 g; 15.0 mmol) in 2M methanolic ammonia (200 mL) was heated under reflux at 70° C. for 24 h. Volatile materials were removed under reduced pressure, the residue was dissolved in minimum quantity of MeOH and slurried with silica gel. The dried slurry was applied to the top of a column of silica and eluted with $CHCl_3$ containing 0.1, 0.2, 0.3, 0.4 and 1.5% of MeOH. Fractions containing the product were pooled and the solvent was removed under reduced pressure to obtain 7e (3.01 g): mp, softens and foams at 117–125° C., decomposes at 142–156° C.; TLC, $R_f$ 0.44 ($CHCl_3$-MeOH—$NH_4OH$, 95:5: 0.5).

EXAMPLE 5

Preparation of 5'-Amino-17-(cyclopropylmethyl)-6,7-didehydro-3,14-dihydroxy-4,5α-epoxypyrido[2',3':6,7]morphinan (7f).

The above nitropyridine (2.9 g, 6.6 mmol) was dissolved in warm EtOH (300 mL). To the solution was added, under an atmosphere of argon, 10% palladium on carbon (0.90 g) and the mixture was hydrogenated at 50 psi in a Paar shaker for 24 h. The mixture was filtered through a pad of celite under argon. The solvent was removed under reduced pressure to obtain 2.67 g of the amino compound 7f as a pure produce. Pm 202–204° C. dec; TLC, $R_f$ 0.34($CHCl_3$-MeOH, 9:1).

EXAMPLE 6

Preparation of 5'-Amino-4'-cyano-17-(cyclopropylmethyl)-6,7-didehydro-3,14-dihydroxy-4,5α-epoxythieno[2',3':7,6] morphinan (8a).

A stirred mixture of naltrexone (1.70 g; 5.0 mmol), malononitrile (0.33 g; 5.0 mmol) and sulfur (0.16 g; 5.0 mmol) in EtOH (10 mL) was treated dropwise with morpholine (0.5 mL; 5.7 mmol) and stirred at room temperature for 24 h.

The mixture was concentrated under reduced pressure and the residue was triturated with water. The water insoluble product was collected by filtration, washed with water and dried. The crude product was purified by flash chromatography over a column of silica using $CHCl_3$-MeOH (95:5) as the eluent to obtain 8a (0.56 g): mp 208–212° C. dec; TLC, $R_f$ 0.53 ($CHCl_3$-MeOH, 9:1).

EXAMPLE 7

Preparation of 5'-Amino-4'-carbomethoxy-17-(cyclopropylmethyl)-6,7-didehydro-3,14-dihydroxy-4,5α-epoxythieno [2',3':7,6]morphinan (8b).

A stirred mixture of naltrexone (1.70 g; 5.0 mmol), methyl cyanoacetate (0.44 mL; 5.0 mmol) and sulfur (0.16 g; 5.0 mmol) in MeOH (10 mL) was treated dropwise at room temperature with morpholine (0.5 mL; 5.7 mmol) and the mixture was then refluxed overnight. The mixture was allowed to cool to room temperature and the solid obtained was collected by filtration. The crude product was purified by flash chromatography over a column of silica using $CHCl_3$-MeOH (98:2) as the eluent to obtain 8b (0.84 g): mp 189–191° C. dec; TLC, $R_f$ 0.51 ($CHCl_3$-MeOH, 9:1).

EXAMPLE 8

Preparation of 5'-Amino-4'-carbethoxy-17-(cyclopropylmethyl)-6,7-didehydro-3,14-dihydroxy-4,5α-epoxythieno[2', 3':7,6]morphinan (8c).

A stirred mixture of naltrexone (1.70 g; 5.0 mmol), ethyl cyanoacetate (0.8 mL; 7.5 mmol) and sulfur (0.24 g; 7.5 mmol) in EtOH (10 mL) was treated dropwise at room temperature with morpholine (0.87 mL; 10.0 mmol) and the mixture was then refluxed overnight. The mixture was allowed to cool to room temperature and poured over ice-water mixture (500 mL). The solid obtained was collected by filtration. The crude product was purified by flash chromatography over a column of silica using $CHCl_3$-MeOH (99:1) as the eluent to obtain 8c (1.1 g): mp 189–191° C. dec; TLC, $R_f$ 0.57 ($CHCl_3$-MeOH, 9:1).

EXAMPLE 9

Preparation of 5'-Amino-4'-benzyloxycarbonyl-17-(cyclopropylmethyl)-6,7-didehydro-3,14-dihydroxy-4,5α-epoxythieno[2',3':7,6]morphinan (8d).

A stirred mixture of naltrexone (1.70 g; 5.0 mmol), benzyl cyanoacetate (1.31 g; 7.5 mmol) and sulfur (0.24 g; 7.5 mmol) in DMF (15 mL) was treated dropwise at room temperature with morpholine (0.66 mL; 7.6 mmol) and the mixture was then heated under reflux at 80° C. for 24 h. The reaction mixture was allowed to cool to room temperature and poured over ice-water mixture. The solid obtained was collected by filtration, washed with water and dried. The crude product was purified by flash chromatography over a column of silica using $CHCl_3$-MeOH (99:1) as the eluent to obtain 8d (1.16 g): mp 208–212° C. dec; TLC, $R_f$ 0.69 ($CHCl_3$-MeOH 9:1).

EXAMPLE 10

Preparation of 5'-Amino-4'-aminocarbonyl-17-(cyclopropylmethyl)-6,7-didehydro-3,14-dihydroxy-4,5α-epoxythieno[2',3':7,6]morphinan (8e).

A stirred mixture of naltrexone (1.70 g; 5.0 mmol), cyanoacetamide (0.63 g; 7.5 mmol) and sulfur (0.24 g; 7.5 mmol) in EtOH (20 mL) was treated dropwise at room temperature with morpholine (0.66 mL; 7.6 mmol) and the mixture was then refluxed for 24 h. After allowing to cool to room temperature, the reaction mixture was poured over ice-water mixture. The solid obtained was collected by filtration, dissolved in $CHCl_3$ and washed with saturated aqueous $NaHCO_3$ followed by water. The organic layer was dried ($Na_2SO_4$), filtered, and the solvent was removed under reduced pressure. The crude product was purified by flash chromatography over a column of silica using $CHCl_3$-MeOH (95:5) as the eluent to obtain 8e (0.82 g): mp 250–264° C. dec; TLC, $R_f$ 0.39 ($CHCl_3$-MeOH, 9:1).

EXAMPLE 11

Preparation of 5'-Amino-4'-benzoyl-17-(cyclopropylmethyl)-6,7-didehydro-3,14-dihydroxy-4,5α-epoxythieno[2',3':7,6]morphinan (8f).

A stirred mixture of naltrexone (1.70 g; 5.0 mmol), benzoyl acetonitrile (0.725 g; 5.0 mmol) and sulfur (0.24 g; 7.5 mmol) in EtOH (12 mL) was treated dropwise at room temperature with morpholine (0.66 mL; 7.6 mmol) and the mixture was then refluxed for 24 h. The reaction mixture was cooled and poured over ice-water mixture. The solid obtained was collected by filtration, washed with water and dried. The crude product was purified by flash chromatography over a column of silica using $CHCl_3$-MeOH (99:1) as the eluent to obtain 8f (0.52 g): mp 190–194° C. dec; TLC, $R_f$ 0.61 ($CHCl_3$-MeOH, 9:1).

EXAMPLE 12

Biological Evaluations.

Radioligand Binding Assays. Mu binding sites were labeled using [$^3$H]DAMGO (1–3 nM). Rat membranes were prepared each day using a partially thawed frozen rat brain which was homogenized with a polytron in 10 mL/brain of ice cold 10 mM Tris-HCl, pH 7.0. Membranes were then centrifuged twice at 30,000 g for 10 min and resuspended with ice-cold buffer following each centrifugation. After the second centrifugation, the membranes were resuspended in 50 mM Tris-HCl, pH 7.4 (50 mL/brain) at 25° C. Incubations proceeded for 2 h at 25° C. in 50 mM Tris-HCl, pH 7.4, along with a protease inhibitor cocktail (PIC). The nonspecific binding was determined using 20 μM of levallorphan. Delta binding sites were labeled using [$^3$]DADLE (2 nM) and rat brain membranes. Rat membranes were prepared each day using a partially thawed frozen rat brain which was homogenized with a polytron in 10 mL/brain of ice cold 10 mM Tris-HCl, pH 7.0. Membranes were then centrifuged twice at 30,000 g for 10 min and resuspended with ice-cold buffer following each centrifugation. After the second centrifugation, the membranes were resuspended in 50 mM Tris-HCl, pH 7.4 (50 mL/brain) at 25° C. Incubations proceeded for 2 h at 25° C. in 50 mM Tris-HCl pH 7.4, containing 100 mM choline chloride, 3 mM $MnCl_2$, and 100 nM DAMGO to block binding to μ sites, and PIC. Nonspecific binding was determined using 20 μM levallorphan. Kappa binding sites were labeled using [$^3$H]U69,593 (2 nM). Guinea pig brain membranes were prepared each day using partially thawed guinea pig brain which was homogenized with a polytron in 10 mL/brain of ice cold 10 mM Tris-HCl pH 7.0. The membranes were then centrifuged twice at 30,000 g for 10 min and resuspended with ice-cold buffer following each centrifugation. After the second centrifugation, the membranes were resuspended in 50 mM Tris-HCl, pH 7.4 (75 mL/brain) at 25° C. Incubations proceeded for 2 h at 25° C. in 50 mM Tris-HCl, pH 7.4, containing 1 μg/mL of captopril and PIC. Nonspecific binding was determined using 1 μM U69,593. Each $^3$H ligand was displaced by 8–10 concentrations of test drug, two times. Compounds were prepared as 1 mM solution with 10 mM Tris buffer (pH 7.4) containing 10% DMSO before drug dilution. All drug dilutions were done at 10 mM Tris-HCl, pH 7.4, containing 1 mg/mL bovine serum albumin. All washes were done with ice-cold 10 mM Tris-HCl, pH 7.4. The $IC_{50}$ and slope factor (N) were obtained by using the program MLAB-PC (Civilized Software, Bethesda, Md.). Ki values were calculated according to the equation $Ki=IC_{50}/(1+[L]/Kd)$.

Bioassays in GPI and MVD smooth muscle preparations. Electrically-induced smooth muscle contractions of mouse vas deferens and strips of guinea pig ileum longitudinal muscle myenteric plexus were used. Tissues came from maile ICR mice weighing 25–40 g and male Hartley guinea pigs weighing 250–500 g. The tissues were tied to gold chain with suture silk, suspended in 20 mL baths containing 37° C. oxygenated (95% $O_2$, 5% $CO_2$) Krebs bicarbonate solution (magnesium free for the MVD), and allowed to equilibrate for 15 min. The tissues were then stretched to optimal length previously determined to be 1 g tension (0.5 g for MVD) and allowed to equilibrate for 15 min. The tissues were stimulated transmurally between platinum wire electrodes at 0.1 Hz, 0.4 ms pulses (2-ms pulses for MVD), and supramaximal voltage. An initial dose-response curve of DPDPE or PL-017 was constructed at the start of each assay to establish tissue effects, allowing each tissue to be used as its own control.

Tissues not producing typical results were not used. Experimental compounds were added to the baths in 14–60 μL volumes. Succeeding doses of argonist were added cumulatively to the bath at 3 minute intervals to produce a concentration-response curve. The tissues were then washed extensively with fresh buffer until the original contraction height was re-established. Agonist effects of the compounds at 1 μM were measured as percent inhibition of contraction height 10 min after addition to the bath. Antagonist effects to DPDPE and PL-017 were assayed after incubation of the tissues with 1 μM concentration of the compound in the bath for 30 minutes. The tissues were then washed with fresh buffer for 30 min, and the agonist dose-response curve was repeated. Rightward shifts in the dose-response curves were calculated by dividing the antagonized dose-response curve $IC_{50}$ value by the unantagoniced $IC_{50}$ value. $IC_{50}$ values represent the mean of two to four tissues. $IC_{50}$ estimates and their associated standard errors were determined by using a computerized nonlinear least-squares method.

The following biological results discussed below were obtained.

The δ, μ and κ opioid receptor binding profile of the pyridomorphinans is given in Table 1, and that of thienomorphinans is given in Table 2. The opioid antagonist and agonist potencies of the target compounds in the MVD and GPI smooth muscle preparations are listed in Table 3. All of the 5'-substituted pyridomorphinans bind with high affinities (Ki<10 nM) at the δ receptor. Although the substituted compounds show slight reduction in binding potencies relative to the parent compound 7a, they retain the δ selective binding profile of the parent compound. The μ/δ and κ/δ selectivity ratios are differentially affected by different substituents. The bromine at the 5'-position (7b) increases δ selectivity by decreasing relative binding potencies at both μ and κ sites. The ester compound 7d on the other hand has increased μ/δ selectivity ratio but lower κ/δ selectivity ratio than the parent compound. The bromo compound, besides being the most potent and δ selective in binding assays, is also the most potent δ antagonist in the MVD with a Ke of (3.1 nM).

All of the thienomorphinans bind with high affinity to the δ receptor (Ki<14 nM). Most of the compounds also bind to the μ and particularly the κ site with high affinity thus leading to generally low binding selectivity ratios. The substituents at the 4'-position (equivalent to the indolic nitrogen position of NTI and BNTI) are tolerated at the δ receptor site equally well despite the differences in the steric bulk of the substituents. Interestingly, compound 8d carrying the bulky benzyl ester substituent shows marginally improved μ/δ and κ/δ selectivity ratios due to decreased binding affinity at the μ and κ receptors. This compound also displays the highest δ antagonist activity in the MVD with a Ke of 5.0 nM and weak agonist activity in the GPI with 40% inhibition at 1 μM concentration. These results indicate that the introduction of substituents on these functionalized frameworks increases binding and antagonist potency at the δ receptor and/or decreases binding and activity at the μ and κ receptors.

TABLE 1

Opioid Receptor Binding Affinities of Pyridomorphinans in Rat or Guinea Pig Brain Membranes

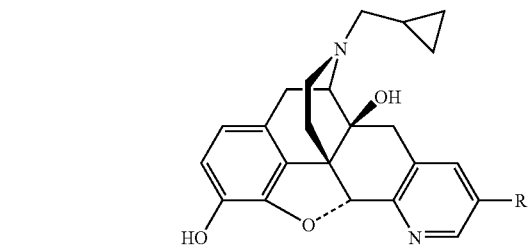

| | | Ki (nM) ± SEM | | | Selectivity Ratio | |
| --- | --- | --- | --- | --- | --- | --- |
| compd. | R | δ[a] | μ[b] | $κ_1$[c] | μ/δ | $κ_1$/δ |
| 7a[d] | H | 0.78 ± 0.06 | 1.5 ± 0.09 | 8.8 ± 0.69 | 1.9 | 11 |
| 7b | Br | 1.2 ± 0.13 | 15.5 ± 1.0 | 55.7 ± 7.0 | 13 | 46 |
| 7c | CN | 4.5 ± 0.28 | 16.0 ± 1.8 | 33.9 ± 2.0 | 3.6 | 7.5 |
| 7d | $CO_2C_2H_5$ | 4.2 ± 0.27 | 37.0 ± 3.4 | 9.6 ± 0.93 | 8.8 | 2.3 |
| 7e | $NO_2$ | 5.5 ± 0.67 | 17.5 ± 2.0 | 92.0 ± 12.8 | 3.2 | 17 |
| 7f | $NH_2$ | 8.0 ± 0.3 | 12.8 ± 0.93 | 12.0 ± 1.2 | 1.6 | 1.5 |

[a]Displacement of [$^3$H]DADLE (1.3–2.0 nM) in rat brain membranes using 100 nM DAMGO to block binding to μ-sites.
[b]Displacement of [$^3$H]DAMGO (1.4–2.0 nM) in rat brain membranes.
[c]Displacement of [$^3$H]U69, 593 (1.2–2.2 nm) in guinea pig brain membranes.
[d]Data taken from Ananthan, S., et al., Synthesis, Opioid Receptor Binding, and Biological Activities of Naltrexone-Derived Pyrido- and Pyrimidomorphinans, J. Med. Chem. 1999, 42, in press.

TABLE 2

Opioid Receptor Binding Affinities of Thienomorphinans in Rat or Guinea Pig Brain Membranes

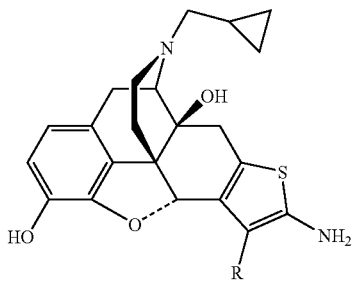

| | | Ki (nM) ± SEM | | | Selectivity Ratio | |
|---|---|---|---|---|---|---|
| compd. | R | δ[a] | μ[b] | κ₁[c] | μ/δ | κ₁δ |
| 8a | CN | 2.6 ± 0.11 | 5.5 ± 0.2 | 1.5 ± 0.12 | 2.1 | 0.6 |
| 8b | CO₂CH₃ | 6.6 ± 0.3 | 29.0 ± 4.0 | 8.7 ± 0.34 | 4.4 | 1.3 |
| 8c | CO₂C₂H₅ | 5.0 ± 0.2 | 20.0 ± 1.0 | 9.0 ± 0.81 | 4.0 | 1.8 |
| 8d | CO₂CH₂C₆H₅ | 7.0 ± 0.3 | 61.0 ± 3.0 | 48.0 ± 3.0 | 8.7 | 6.9 |
| 8e | CONH₂ | 3.7 ± 0.2 | 21.0 ± 1.3 | 2.0 ± 0.2 | 5.7 | 0.5 |
| 8f | COC₆H₅ | 14.0 ± 0.7 | 50.0 ± 3.0 | 14.0 ± 0.7 | 3.6 | 1.0 |

[a]Displacement of [$^3$H]DADLE (1.3–2.0 nM) in rat brain membranes using 100 nM DAMGO to block binding to μ-sites.
[b]Displacement of [$^3$H]DAMGO (1.4–2.0 nM) in rat brain membranes.
[c]Displacement of [$^3$H]U69, 593 (1.2–2.2 nm) in guinea pig brain membranes.

TABLE 3

Opioid Antagonist and Agonist Potencies of Pyrido- and Thienomorphinans in the MVD and GPI Preparations

| | antagonist activity | | | | | agonist activity | |
|---|---|---|---|---|---|---|---|
| | DPDPE (δ)[a] MVD | | PL017 (μ)[b] GPI | | K$_e$ selectivity | MVD IC$_{50}$ (nM) or % | GPI IC$_{50}$ (nM) or % |
| No | IC$_{50}$ ratio | K$_e$ nM[c] | IC$_{50}$ ratio | K$_e$ nM[c] | ratio μδ | max resp[d] | max resp[d] |
| 7a[e] | 27.9 ± 1.2 | 37 | 7.08 ± 3.44 | 164 | 4.4 | 0% | 0% |
| 7b | 325 ± 127 | 3.1 | 43.9 ± 25.6 | 23 | 14 | 0% | 0% |
| 7c | 23.6 ± 2.2 | 44 | 2.2 ± 1.1 | f | — | 0% | 0% |
| 7d | 50.1 ± 4.9 | 20 | 14.5 ± 5.2 | 74 | 3.7 | 0% | 0% |
| 7e | 20.7 ± 4.2 | 51 | 4.7 ± 0.59 | 271 | 5.3 | 14% | 0% |
| 7f | 43.3 ± 9.0 | 26 | 23.4 ± 4.8 | 49 | 1.9 | 6% | 0% |
| 8a | 109.6 ± 12.1 | 9.6 | 160.3 ± 41.6 | 8.7 | 0.9 | 0% | 0% |
| 8b | 53.5 ± 10.1 | 21 | 39.1 ± 11.6 | 35 | 1.7 | 0% | 0% |
| 8c | 19.8 ± 6.6 | 68 | 46.0 ± 21.9 | 26 | 0.4 | 11% | 0% |
| 8d | 289 ± 13 | 5.0 | g | — | — | 11% | 40% |
| 8e | 118.6 ± 38.4 | 10 | 47.8 ± 10.7 | 24 | 2.4 | 5% | 4% |
| 8f | 24.4 ± 4.0 | 46 | 21.6 ± 7.7 | 62 | 1.3 | 15% | 25% |

[a]DPDPE as the agonist.
[b]PL-017 as the agonist.
[c]Kc (nM) = [antagonist]/(IC$_{50}$ ratio − 1), where the IC$_{50}$ ratio is the IC$_{50}$ of the agonist in the presence of antagonist divided by the control IC$_{50}$ in the same preparation (n = 3).
[d]Agonist activity, percentage inhibition of contraction at 1 μM.
[e]Data for 7a included for comparison. Data taken from Ananthan et al., supra.
f The agonist effects precluded the determination of antagonist effects.
g IC$_{50}$ ratio was not statistically different from 1.

The pharmaceutically acceptable effective dosage of the active compound of the present invention to be administered is dependent on the species of the warm-blooded animal (mammal), the body weight, age and individual condition, and on the form of administration.

The pharmaceutical composition may be oral, parenteral, suppository or other form which delivers the compounds used in the present invention into the bloodstream of a mammal to be treated.

The compounds of the present invention can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms, the kind of concurrent treatment; the frequency of treatment; and the effect desired. A daily dosage of active ingredient can be expected to be about 0.001 to 1000 milligram (mg) per kilogram (kg) of body weight, with the preferred dose being 0.1 to about 30 mg/kg.

Dosage forms (compositions suitable for administration) typically contain from about 1 mg to about 100 mg of active ingredient per unit. In these pharmaceutical compositions, the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms. The active ingredient can also be administered intranasally (nose drops) or by inhalation.

Other dosage forms are potentially possible such as administration transdermally, via a patch mechanism or ointment.

Gelatin capsules contain the active ingredient and powdered carriers, such as lactose, starch, cellulose derivatives, magnesium stearate, stearic acid, and the like.

Similar diluents can be used to make compressed tablets. Both tablets and capsules can be manufactured as sustained release products to provide for continuous release of medication over a period of hours. Compressed tablets can be sugar-coated or film-coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water-soluble salt of the active ingredient, suitable stabilizing agents, and, if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in Remington's Pharmaceutical Sciences, Mack Publishing Company, a standard reference text in this field.

Useful pharmaceutical dosage forms for administration of the compounds according to the present invention can be illustrated as follows:

Capsules

A large number of unit capsules are prepared by filling standard two-piece hard gelatin capsules each with 100 mg of powdered active ingredient, 150 mg of lactose, 50 mg of cellulose, and 6 mg of magnesium stearate.

Soft Gelatin Capsules

A mixture of active ingredient in a digestible oil such as soybean oil, cottonseed oil, or olive oil is prepared and injected by means of a positive displacement pump into gelatin to form soft gelatin capsules containing 100 mg of the active ingredient. The capsules are washed and dried.

Tablets

A large number of tablets are prepared by conventional procedures so that the dosage unit was 100 mg of active ingredient, 0.2 mg of colloidal silicon dioxide, 5 mg of magnesium stearate, 275 mg of microcrystalline cellulose, 11 mg of starch, and 98.8 mg of lactose. Appropriate coatings may be applied to increase palatability or delay absorption.

Various modifications of the invention in addition to those shown and described herein will be apparent to those skilled in the art from the foregoing description. Such modifications are also intended to fall within the scope of the appended claims.

The foregoing disclosure includes all the information deemed essential to enable those skilled in the art to practice the claimed invention. Because the cited applications may provide further useful information, these cited materials are hereby incorporated by reference in their entirety.

The foregoing description of the invention illustrates and describes the present invention. Additionally, the disclosure shows and describes only the preferred embodiments of the invention but, as mentioned above, it is to be understood that the invention is capable of use in various other combinations, modifications, and environments and is capable of changes or modifications within the scope of the inventive concept as expressed herein, commensurate with the above teachings and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

What is claimed is:

1. A compound represented by the formula:

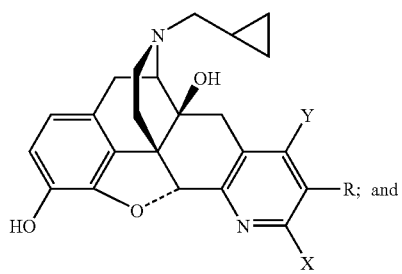

wherein each of Y, X and R individually is selected from the group consisting of hydrogen, hydroxyl, halo, $CF_3$, $NO_2$, CN, $NH_2$, $COR^1$ and $CO_2R^2$ wherein $R^1$ is selected from the group consisting of alkyl, aryl, alkaryl, and $NH_2$, and $R^2$ is selected from the group consisting of alkyl, aryl, and aralkyl, and provided that at least one of Y, X and R in formula I is other than hydrogen; or pharmaceutically acceptable salt thereof.

2. The compound of claim 1 represented by formula I wherein X is H, Y is H and R is Br.

3. The compound of claim 1 represented by formula I wherein X is H, Y is H and R is CN.

4. The compound of claim 1 represented by formula I wherein X is H, Y is H and R is $CO_2R^2$.

5. The compound of claim 1 represented by formula I wherein X is H, Y is H and R is $NO_2$.

6. The compound of claim 1 represented by formula I wherein X is H, Y is H and R is $NH_2$.

* * * * *